United States Patent [19]

LaGrange et al.

[11] Patent Number: 5,468,472
[45] Date of Patent: Nov. 21, 1995

[54] TOPICAL PROCESS FOR LIGHTENING THE SKIN OR TREATING PIGMENTAL BLEMISHES USING A COMPOSITION CONTAINING 4-THIORESORCIN DERIVATIVES

[75] Inventors: Alain LaGrange, Coupvray; Hervé Borowiak, Sevran, both of France

[73] Assignee: L'Oreal, Paris, France

[21] Appl. No.: 234,555

[22] Filed: Apr. 28, 1994

[30] Foreign Application Priority Data

May 6, 1993 [FR] France ................... 93 05452

[51] Int. Cl.$^6$ ................... A61K 7/00; A61K 9/127; A61K 7/48
[52] U.S. Cl. ................... 424/62; 424/401; 424/450; 424/489; 424/59; 514/944
[58] Field of Search ................... 424/62, 401, 450, 424/489, 59; 514/944

[56] References Cited

U.S. PATENT DOCUMENTS 4,990,330  2/1991  Oyame ................... 424/59

FOREIGN PATENT DOCUMENTS 0341664  11/1989  European Pat. Off. .
61-27909  2/1986  Japan .
3109319  5/1991  Japan .

OTHER PUBLICATIONS

Chemical Abstracts, vol. 118, No. 22, May 31, 1993, Abstract No. 219474w.

Primary Examiner—Gollamudi S. Kishore

Attorney, Agent, or Firm—Oliff & Berridge

[57] ABSTRACT

A topical process for lightening the skin or treating pigmental blemishes consisting in applying to the part of the skin to be treated a composition containing, as active compounds, 4-thioresorcin derivatives corresponding to the following formula:

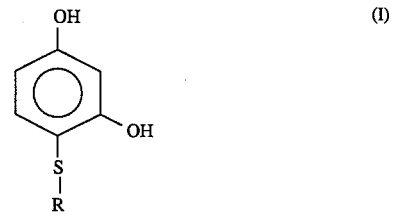

wherein:

R represents a $C_1$–$C_6$ alkyl radical, a $C_1$–$C_6$ haloalkyl radical, an aryl radical, an aralkyl radical which is unsubstituted or substituted by a lower alkyl or lower alkoxy radical or a halogen atom, the radical —$C_nH_{2n}$—COOR' where n is an integer between 1 and 5 and R' represents a $C_1$–$C_6$ alkyl radical, a morpholinoalkyl or piperidinoalkyl radical in which the alkyl radical is $C_1$–$C_6$, or the radical

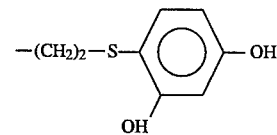

9 Claims, No Drawings

TOPICAL PROCESS FOR LIGHTENING THE SKIN OR TREATING PIGMENTAL BLEMISHES USING A COMPOSITION CONTAINING 4-THIORESORCIN DERIVATIVES

The subject of the present invention is a topical process for lightening the skin or treating pigmental blemishes by applying to the skin a composition containing 4-thioresorcin derivatives.

It will be recalled that the mechanism of formation of skin pigmentation, that is to say of the formation of melanins, is particularly complex and involves, schematically, the following main stages:

Tyrosine→Dopa→Dopaquinone→Dopachrome→Melanins the enzyme which takes part in this sequence of reactions being essentially tyrosinase.

The substances which are the most used as depigmenting agents are currently more particularly hydroquinone and its derivatives, in particular its ethers such as hydroquinone monomethyl ether.

These compounds, if they have some effectiveness, are unfortunately not free of side effects which can make their use problematic or indeed dangerous.

Thus, hydroquinone, the use of which is moreover restricted to a concentration of 2%, is a particularly irritating and cytotoxic compound for melanocytes and its complete or partial replacement has been envisaged by many writers.

U.S. Pat. No. 4,526,179 has thus proposed certain fatty esters of hydroquinone which have good activity and which are less irritating and more stable than hydroquinone.

Likewise, Japanese Application N° 27909/86 has proposed other hydroquinone derivatives which do not have the disadvantages of hydroquinone but whose effectiveness has proved to be relatively poor.

It is well established that a substance exerts a depigmenting action if it acts directly on the vitality of the epidermal melanocytes where melanogenesis normally takes place and/or if it interferes with one of the stages in the biosynthesis of melanins, either by inhibiting one of the enzymes involved or by being inserted as a structural analogue in the synthetic route which can thus be blocked, hence the depigmenting effect.

By application of this principle, the use of compounds such as 4-alkylresorcins was thus proposed in Patent Application EP-0,341,664.

The use of topical depigmenting substances which are highly effective and inoffensive is very particularly sought after with a view to treating regional hyperpigmentations by melanocytic hyperactivity such as idiopathic melasmas, arising during pregnancy ("mask of pregnancy" or chloasma) or as a consequence of oestrone/progestogen contraception, localized hyperpigmentations by benign melanocytic hyperactivity and proliferation such as senile pigmental blemishes known as actinic lentigo, accidental hyperpigmentations such as photosensitization and post-lesional scarring, as well as certain leucodermas such as vitiligo where, for want of being able to repigment the damaged skin, the end result is to depigment the remaining normal skin regions to give the whole skin a homogeneous whitish tint.

After many studies on different substances, it was now very surprisingly observed that other types of resorcin derivatives, in particular 4-thioresorcin derivatives or 4-thio-1,3-dihydroxybenzene derivatives, carrying various substituents on the sulphur atom, also had an excellent depigmenting action which, for the most part, has proved to be better than that of hydroquinone in the "in vitro" inhibition test of the tyrosinase activity as will be described below.

The subject of the present invention is a topical process for lightening the skin or treating pigmental blemishes consisting in applying to the pat of the skin to be treated a cosmetic or dermatologic composition containing as active compounds, 4-thioresorcin derivatives corresponding to the following general formula:

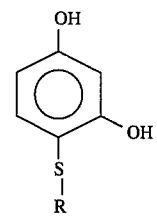

in which:

R represents a $C_1$–$C_6$ alkyl radical, a $C_1$–$C_6$ haloalkyl radical, an aryl radical, an aralkyl radical which is unsubstituted or substituted by a lower alkyl or lower alkoxy radical or a halogen atom, the radical —$C_nH_{2n}$—COOR' where n is an integer between 1 and 5 and R' represents a $C_1$–$C_6$ alkyl radical, a morpholinoalkyl or piperidinoalkyl radical in which the alkyl radical is $C_1$–$C_6$, or the radical

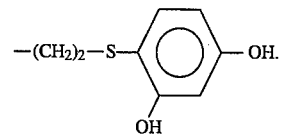

According to the invention, the halogen atom is preferably chosen from chlorine and fluorine.

The aryl radical is preferably the phenyl radical and the aralkyl radical is preferably the benzyl radical.

Mention may be made, among the compounds of formula (I), of especially the following:

4-(methylthio)resorcin,
4-(ethylthio)resorcin,
4-(n-butylthio)resorcin,
4-(n-propylthio)resorcin,
4-(isopropylthio)resorcin,
4-(ethoxycarbonylmethylthio)resorcin,
4-(ethoxycarbonylisopropylthio)resorcin,
4-(benzylthio)resorcin,
4-(phenylthio)resorcin,
4-(4'-methoxybenzylthio)resorcin,
4-(4'-chlorobenzylthio)resorcin,
4-(4'-methylbenzylthio)resorcin,
4-(3'-morpholinopropylthio)resorcin,
4-(4'-morpholinobutylthio)resorcin,
4-(4'-piperidinobutylthio)resorcin,
4-(4'-chlorobutylthio)resorcin,
4-(2',2'-dichloro-1',1',2'-trifluoroethylthio)resorcin, and
1,2-bis(2',4'-dihydroxyphenylthio)ethane.

Mention may be made, among the particularly preferred compounds, of especially:

4-(methylthio)resorcin,
4-(ethylthio)resorcin,
4-(n-propylthio)resorcin,
4-(isopropylthio)resorcin,
4-(benzylthio)resorcin,
1,2-bis(2',4'-dihydroxyphenylthio)ethane
4-(3'-morpholinopropylthio)resorcin, and 4-(ethoxycarbonylmethylthio)resorcin.

The concentration of compounds of formula (I) in the depigmenting compositions used according to the invention process is generally between 0.01% and 10% and preferably between 0.5% and 5% by weight with respect to the total weight of the composition.

The vehicle of the compositions can be in particular an aqueous or aqueous/alcoholic solution, an emulsion of oil-in-water or water-in-oil type, an emulsified gel or alternatively a two-phase system.

The compositions used according to the invention process are preferably provided in the form of a lotion, of a cream, of a milk, of a gel, of a mask, of microspheres or nanospheres or of vesicular dispersions. In the case of vesicular dispersions, the constituent lipids of the vesicles can be of ionic or non-ionic type or else a mixture of these.

These cosmetic compositions can also contain a humectant, a surface agent, a keratolytic agent, an anti-inflammatory agent, a complexing agent, an anti-oxidizing agent, a preserving agent, a fragrance or a sunscreen.

These compositions are applied topically to the part of the skin to be treated in an amount corresponding to the usual application doses for the type of composition under consideration (gel, cream, lotion, and the like). For example, in the case of a cream, from 0.5 to 3 mg and in particular from 1 to 2 mg of cream per cm$^2$ of skin and per application are used, at the rate of one or two applications per day.

The compounds of general formula (I) are known, with the exception of 4-(isopropylthio)resorcin, 1,2-bis(2',4'-dihydroxyphenylthio)ethane and 4-(3-morpholinopropylthio)resorcin, and are obtained according to conventional methods of synthesis. The new compounds mentioned above can be prepared by opening the tioxolone, in basic medium, and alkylation with the corresponding halide.

Their process of preparation is described in more detail below.

"In vitro" Studies

Some of the compounds of general formula (I) have been studied in comparison with an equivalent molar amount of hydroquinone in the in vitro inhibition test of the activity of tyrosinase.

According to this test, the amount of dopachrome formed during the chain of reactions of conversion of tyrosine to melanins is monitored by visible spectrometry at 475 nm. These reactions are catalyzed in vitro by fungal tyrosinase, in the presence of a reducing co-substrate (for example, a small amount of L-dopa) in order to initiate the hydroxylation reaction of L-tyrosine to L-dopa, which is then catalytically oxidized to dopaquinone and then to dopachrome, an intermediate product before the non-enzymatic oxidation reactions which result in the formation of melanins.

The concentration of dopachrome formed with time in the presence and in the absence of the inhibitor thus measured.

The inhibitor concentrations are set at 50 mol % with respect to the concentration of tyrosine in the reaction medium.

The inhibition effect is expressed by the lowering in the maximum amount of dopachrome formed (optical density value at 475 nm read at the plateau of the curve) with respect to the amount obtained in the absence of inhibitor.

Experimental Protocol

Reagents:

A - 0.1M Phosphate buffer, pH=6.5 (1% Tween 20)

B - $2.10^{-3}$ M Mother solution of L-tyrosine in A

C - $10^{-4}$ M Mother solution of L-dopa in A

D - Mother solution of fungal tyrosinase in A containing 2,400 units/ml

E - $10^{-2}$ M Mother solution of the inhibitor in A (Solutions C and D are to be prepared on the day)

Results:

| reference cell: | 3 ml of A |
|---|---|
| test cell: | 1 ml of B |
| | 0.1 ml of C |
| | 1.85 ml of A + E | homogenize and equilibrate at 25° C.

add 0.05 ml of D mix rapidly and observe the kinetics by measuring the absorbence at 475 nm as a function of time.

TABLE I

| Compounds | % inhibition |
|---|---|
| 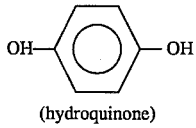 (hydroquinone) | −33% |
| 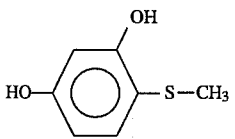 | −90% |
| 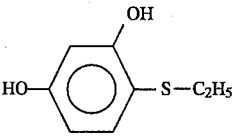 | −88% |
| 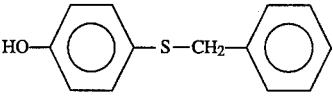 | −95% |
| 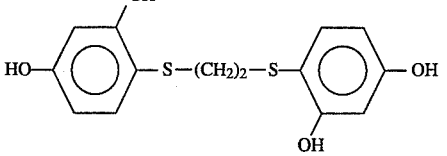 | −79% |
| 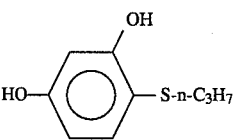 | −76% |
| 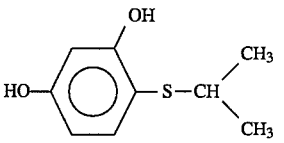 | −84% |

TABLE I-continued

| Compounds | % inhibition |
|---|---|
| OH / HO-〇-S—CH₂CO₂C₂H₅ | −94% |
| OH / HO-〇-S—(CH₂)₃—N(morpholine) | −65% |

EXAMPLES OF PREPARATION OF THE COMPOUNDS

Example 1: Preparation of 4-(isopropylthio)resorcin 8.4 g of tioxolone (1 eq) are added to an aqueous sodium hydroxide solution (3.5 eq) (6.7 g of sodium hydroxide in 84 ml of water) at room temperature. After complete dissolution (30 minutes), 5.5 ml of isopropyl iodide are added. After stirring for two hours at room temperature, the mixture is acidified with hydrochloric acid and then extracted with ethyl ether. The organic phases are washed, dried and evaporated. The residue is recrystallized from an alcohol/water mixture to obtain pale-yellow crystals having a melting point of: 67° C.

Elemental analysis: $C_9H_{12}O_2S$

|  | C % | H % | O % | S % |
|---|---|---|---|---|
| Calculated | 58.67 | 6.56 | 17.37 | 17.4 |
| Found | 59.58 | 6.62 | 17.43 | 16.52 |

Example 2: Preparation of 1,2-bis(2',4'-dihydroxyphenylthio)ethane

The same procedure as in Example 1 is used, from:

33.6 g of tioxolone,
26.8 g of sodium hydroxide pellets,
335 ml of water, and
18.8 g of 1,2-dibromoethane.

After recrystallization from an alcohol/water mixture, dark-beige crystals are obtained with a melting point of: 164° C.

Elemental analysis: $C_{14}H_{14}O_4S_2$

|  | C % | H % | O % | S % |
|---|---|---|---|---|
| Calculated | 54.17 | 4.54 | 20.62 | 20.66 |
| Found | 53.71 | 5.11 | 21.03 | 20.11 |

Example 3: Preparation of 4-(3-morpholinopropylthio)resorcin (1) Preparation of 4-(3-chloropropylthio)resorcin
The same procedure as in Example 1 is used, from:

16.8 g of tioxolone,
33.5 ml of 10N sodium hydroxide solution,
135 ml of water, and
17.3 g of 1-bromo-3-chloropropane.

A pale-yellow oil is obtained which is used directly in the following stage.

Elemental analysis: $C_9H_{11}ClO_2S$

|  | C % | H % | S % |
|---|---|---|---|
| Calculated | 49.13 | 5.07 | 14.66 |
| Found | 48.96 | 4.92 | 14.28 |

(2) Preparation of 4-(3-morpholinopropylthio)resorcin 4 g of 4-(3-chloropropylthio)resorcin and 8 ml of morpholine are heated for two hours at 100° C. The mixture is poured into ice-cold water and extracted with ethyl acetate. The organic phases are washed, dried and concentrated under vacuum. The yellow oil is crystallized from ethyl acetate to lead to white crystals having a melting point of: 99° C.

Elemental analysis: $C_{13}H_{19}NO_3S$

|  | C % | H % | N % | O % | S % |
|---|---|---|---|---|---|
| Calculated | 57.97 | 7.11 | 5.2 | 17.82 | 11.9 |
| Found | 57.59 | 6.75 | 5.08 | 18.53 | 11.76 |

COMPOSITION EXAMPLES

Example 1: Depigmenting Cream

| | |
|---|---|
| 4-(Methylthio)resorcin | 2.8 g |
| Cetylstearyl alcohol oxyethylenated with 20 mol of ethylene oxide | 1 g |
| Glycol monostearate | 3 g |
| Mixture of copra caprylate and caprate | 5 g |
| Cross-linked acrylic acid polymer sold under the name "Carbomer 934P" by the Company Goodrich | 0.3 g |
| Triethanolamine | 0.9 g |
| Ethanol | 20 g |
| Glycerol | 3 g |
| Fragrance, preserving agents q.s. | |
| Water q.s. for | 100 g |

In this example, 4-(methylthio)resorcin can be replaced by 2.0 g of 1,2-bis(2',4'-dihydroxyphenylthio)ethane.

2: Depigmenting Lotion

| | |
|---|---|
| 4-(Methylthio)resorcin | 2.8 g |
| Ethanol | 50 g |
| Polyethylene glycol 400 | 30 g |
| Ethoxydiglycol | 5 g |
| Glycerol | 5 g |
| Water q.s. for | 100 g |

In this example, 4-(methylthio)resorcin can be replaced by 2.5 g of 4-(benzylthio)resorcin.

Example 3: Depigmenting Cream

| | |
|---|---|
| 4-(Methylthio)resorcin | 2.5 g |
| Glycerol | 5.0 g |
| Cyclic dimethylpolysiloxane | 20 g |
| Mixture of oxyethylenated and oxy-propylenated polycetyldimethylsiloxane, of polyglyceryl isostearate containing 4 mol of glycerol and of hexyl laurate sold under the name "Abil W09" by the Company Goldschmidt | 3.0 g |
| Fragrance, preserving agents q.s. | |
| Water q.s. for | 100 g |

In this example, 4-(methylthio)resorcin can be replaced by 1.8 g of 4-(3-morpholinopropylthio)resorcin.

We claim:

1. A topical process for lightening the skin or treating pigmental blemishes consisting in applying to the part of the skin to be treated a composition containing an effective amount sufficient to lighten the skin or treat pigmental blemishes of a 4-thioresorcin derivative corresponding to the following formula:

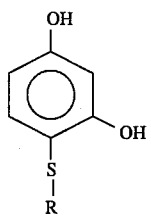
(I)

wherein:

R represents a $C_1-C_6$ alkyl radical, a $C_1-C_6$ haloalkyl radical, an aryl radical, an aralkyl radical which is unsubstituted or substituted by a lower alkyl or lower alkoxy radical or a halogen atom, the radical —$C_nH_{2n}$—COOR' where n is an integer between 1 and 5 and R' represents a $C_1-C_6$ alkyl radical, a morpholinoalkyl or piperidino-alkyl radical in which the alkyl radical is $C_1-C_6$, or the radical

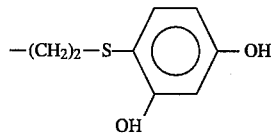

2. The process of claim 1, wherein said aryl radical is phenyl radical.

3. The process of claim 1, wherein said aralkyl radical is benzyl radical.

4. The process of claim 1, wherein said 4-thioresorcin derivatives of forumla (I) are selected from the group consisting of:

4-(methylthio)resorcin,
4-(ethylthio)resorcin,
4-(n-butylthio)resorcin,
4-(n-propylthio)resorcin,
4-(isopropylthio)resorcin,
4-(ethoxycarbonylmethylthio)resorcin,
4-(ethoxycarbonylisopropylthio)resorcin,
4-(benzylthio)resorcin,
4-(phenylthio)resorcin,
4-(4'-methoxybenzylthio)resorcin,
4-(4'-chlorobenzylthio)resorcin,
4-(4'-methylbenzylthio)resorcin,
4-(3'-morpholinopropylthio)resorcin,
4-(4'-morpholinobutylthio)resorcin,
4-(4'-piperidinobutylthio)resorcin,
4-(4'-chlorobutylthio)resorcin,
4-(2',2'-dichloro-1',1',2'-trifluoroethylthio)resorcin, and
1,2-bis(2',4'-dihydroxyphenylthio)ethane 5. The process of claim 4, wherein said 4-thioresorcin derivatives of formula (I) are selected from the group consisting of:

4-(methylthio)resorcin,
4-(ethylthio)resorcin,
4-(n-propylthio)resorcin,
4-(isopropylthio)resorcin,
4-(benzylthio)resorcin,
1,2-bis(2',4'-dihydroxyphenylthio)ethane,
4-(3'-morpholinopropylthio)resorcin, and
4-(ethoxycarbonylmethylthio)resorcin.

6. The process of claim 1, wherein the concentration of said 4-thioresorcin derivatives of formula (I) in the composition is between 0.01% and 10% by weight with respect to the total weight of the composition.

7. The process of claim 6, wherein the concentration of said 4-thioresorcin derivatives of formula (I) in the composition is between 0.5% and 5% by weight with respect to the total weight of the composition.

8. The process of claim 1, wherein the said cosmetic or dermatological composition is selected from the group consisting of a lotion, a cream, a milk, a gel, a mask, microspheres, nanospheres and vesicular dispersions.

9. The process of claim 1, wherein said cosmetic or dermatological composition further contains a cosmetically or dermatologically ingredient selected from the group consisting of a humectant, a surface active agent, a keratolytic agent, an anti-inflammatory agent, an anti-oxidant, a preserving agent, a fragrance and a sunscreen.

* * * * *

UNITED STATES PATENT AND TRADEMARK OFFICE
CERTIFICATE OF CORRECTION

PATENT NO. : 5,468,472
DATED : November 21, 1995
INVENTOR(S) : Alain LaGRANGE et al.

It is certified that error appears in the above-indentified patent and that said Letters Patent is hereby corrected as shown below:

On title page,

Item [75], please change the second named inventor's firs name "Herv"" to --Herve--.

Signed and Sealed this

Twenty-seventh Day of February, 1996

*Attest:*

BRUCE LEHMAN

*Attesting Officer*     Commissioner of Patents and Trademarks